US006503240B1

(12) United States Patent
Niedospial, Jr. et al.

(10) Patent No.: US 6,503,240 B1
(45) **Date of Patent: *Jan. 7, 2003**

(54) VIAL ACCESS ADAPTER

(75) Inventors: John J. Niedospial, Jr., Burlington, NJ (US); Jacqueline M. Kline, Newtown, PA (US); Michael N. Eakins, East Windsor, NJ (US); Ernest Balestracci, Iselin, NJ (US)

(73) Assignee: Brocco Diagnostics, Inc., Princeton, NJ (US)

( * ) Notice: Subject to any disclaimer, the term of this patent is extended or adjusted under 35 U.S.C. 154(b) by 240 days.

This patent is subject to a terminal disclaimer.

(21) Appl. No.: 09/665,090

(22) Filed: Sep. 20, 2000

Related U.S. Application Data

(63) Continuation-in-part of application No. 09/489,619, filed on Jan. 24, 2000, now Pat. No. 6,139,534.

(51) Int. Cl.[7] ................................................ A61B 19/00
(52) U.S. Cl. ........................ 604/411; 604/403; 604/414
(58) Field of Search ................................ 604/411, 403, 604/414, 405, 406, 415, 905, 533, 326; 215/247–249, DIG. 3

(56) References Cited

U.S. PATENT DOCUMENTS

| | | | | |
|---|---|---|---|---|
| 3,359,977 A | | 12/1967 | Burke | |
| 3,608,550 A | | 9/1971 | Stawski | |
| 3,783,895 A | | 1/1974 | Weichselbaum | |
| 4,211,588 A | | 7/1980 | Raines | |
| 4,262,671 A | | 4/1981 | Kersten | |
| 4,505,709 A | | 3/1985 | Froning et al. | |
| 4,588,403 A | | 5/1986 | Weiss et al. | |
| 4,655,763 A | | 4/1987 | Malcolm et al. | |
| 4,787,898 A | | 11/1988 | Raines | |
| 4,834,744 A | * | 5/1989 | Ritson | 604/411 |
| 4,857,068 A | * | 8/1989 | Kahn | 604/126 |
| 4,997,429 A | * | 3/1991 | Dickerhoff et al. | 604/405 |
| 5,358,501 A | | 10/1994 | Meyer | |
| 5,636,660 A | | 6/1997 | Pfleiderer et al. | |
| 6,120,490 A | * | 9/2000 | Neftel | 604/411 |
| 6,139,534 A | * | 10/2000 | Niedospial et al. | 604/403 |

* cited by examiner

*Primary Examiner*—Angela D. Sykes
*Assistant Examiner*—Leslie R. Deak
(74) *Attorney, Agent, or Firm*—Imre Balogh

(57) ABSTRACT

A vial access adapter for withdrawal of a medical fluid contained in a vial which includes a vial access adapter body having a circular top wall with a plurality of vent holes, a circular second wall spaced from the top wall, and a cylindrical side wall which walls define a chamber for holding an anti-bacterial filter. A first spike centrally located in the vial access adapter body extends through the top wall, chamber, and bottom wall, with one end extending above the top wall terminating in a threaded luer connector, while the other end terminates in a sharp point. A flow channel extends through the first spike designed for withdrawal of the medical fluid from the vial. A second spike positioned parallel to the first spike and is integral with the first spike extends from the second wall, one end of which extends into the chamber, and the other end terminates in a sharp point co-joined with the sharp point of the first spike. A flow channel extends through the second spike designed for air flow from the chamber into the vial. An elastomeric membrane positioned within the threaded luer connector seals the opening in the vial access adapter. Preferably the elastomeric membrane is of M-shaped configuration capable of flexing under pressure and of re-sealing itself after being pierced by a luer connector or a syringe equipped with a luer connector.

21 Claims, 14 Drawing Sheets

VIAL ACCESS ADAPTER

This application is a continuation-in-part of application Ser. No. 09/489,619 filed on Jan. 24, 2000, now U.S. Pat. No. 6,139,534.

BACKGROUND OF THE INVENTION

1. Field of the Invention

This invention relates to a vial access adapter connectable to a vial which contains a medical fluid therein and is closed by an elastomeric stopper, wherein the vial access adapter is provided with a dual spike, one for withdrawing the medical fluid from the vial, and the other for simultaneous entry of air into the vial.

2. Reported Developments

Vials made of glass or polymeric materials, the walls of which are non-collapsible, require an air inlet when medical fluid is withdrawn therefrom to prevent the formation of vacuum therein. Typically, vials containing a medical fluid are closed by rubber stoppers which are pierced by a dual spike having a medical fluid passage and an air inlet passage, therein. The air inlet passage contains a filter to prevent entry of particulate matter or bacteria into the vials during the medicament withdrawal process.

The prior art has provided devices comprising a liquid flow passage and an air flow passage, such as disclosed, for example, in U.S. Pat. Nos. 3,359,977, 3,608,550, 3,783,895, 4,262,671, 4,505,709, 4,588,403, 4,787,898, 5,358,501, and 5,636,660. These inventions have advanced the prior art by providing convenient adapters and transfer devices connectable to containers of medical fluids.

In addition to providing in a vial access adapter a dual spike for withdrawing a medical fluid from a vial and simultaneously introducing filtered atmospheric air into the vial, the present invention also provides an elastomeric seal positioned in the fluid passage flow of the dual spike for hermetically sealing the fluid flow passage. In a preferred embodiment the elastomeric seal is of an M-shaped configuration through which the medical fluid can be accessed repeatedly. After each withdrawal of the desired amount the medical fluid the elastomeric seal reseals itself thereby preventing contamination of the medical fluid by air-born particles, such as dust and bacteria.

A further improvement in the present invention over the prior art is the spatial configuration of the medical fluid access spike which, on positioning of the vial access adapter over a vial having a rubber stopper, penetrates the rubber stopper and just clears the bottom surface of the rubber stopper. This spatial configuration allows essentially complete withdrawal of the medical fluid contained in the vial.

SUMMARY OF THE INVENTION

In accordance with the present invention, there is provided a vial access adapter for use with a glass vial or a rigid or semi-rigid polymeric vial containing a liquid medicament, diagnostic agent, or nutritional formulation therein. In the first embodiment of the present invention the vial access adapter body comprises:

- a horizontal top wall having a plurality of vent holes therein;
- a horizontal second wall spaced parallel from the horizontal top wall;
- a cylindrical side wall integral with the horizontal top wall and the horizontal second wall enclosing a chamber therebetween and extending downward from the horizontal second wall forming a skirt and terminating in a bottom rim;

- a first spike centrally located in the vial access adapter body having a top portion extending above the horizontal wall and terminating in an externally threaded luer connector, and a bottom portion extending downward and terminating in a sharp point;
- a fluid flow channel in the first spike designed for carrying the liquid medicament;
- a second spike positioned parallel to the first spike extending downward from the horizontal second wall and terminating in a sharp point;
- an air flow channel in the second spike designed for air flow from the chamber between the horizontal top wall and the horizontal second wall into the vial during withdrawal of the liquid medicament from the vial; and
- an elastomeric membrane within the luer connector for sealing the fluid flow channel.

Preferably, the elastomeric membrane reseals itself upon repeated penetration by an external luer connector and allows repeated withdrawal of the liquid medicament from the vial without risk of contamination from atmospheric environment.

In the second embodiment, the vial access adapter body comprises:

- a vertical cylindrical side wall having a top portion terminating in a top rim, and a skirt portion extending downward from the top rim and terminating in a bottom rim;
- a horizontal, circular wall enclosing the top portion of the cylindrical side wall and is located slightly below the top rim forming a disc-shaped chamber with the top rim;
- a disc-shaped anti-bacterial filter positioned in the disc-shaped chamber;
- a removable retaining disc for the anti-bacterial filter positioned on top of the anti-bacterial filter and having a plurality of vent holes therein;
- a pair of spikes integral with each other and centrally located in the vial access adapter body: the first spike of the pair having a top portion extends above the horizontal, circular wall and the and the removable retaining disc terminating in an externally threaded luer connector and the bottom portion extending downward and terminating slightly below the bottom rim of the cylindrical side wall; and the second spike of the pair extends from the horizontal, circular wall downward to the bottom rim of the cylindrical side wall and terminating slightly below the bottom rim of the cylindrical side wall, wherein the pair of spikes together terminate in a sharp point;
- a fluid flow channel in the first spike of the pair designed to carry a liquid medicament;
- an air flow channel in the second spike of the pair designed for outside air flow from the disc-shaped chamber through the anti-bacterial filter into the vial during withdrawal of the liquid medicament from the vial; and
- an elastomeric membrane within the luer connector of the first spike of the pair for sealing the fluid flow channels.

Preferably, the elastomeric membrane reseals itself upon repeated penetration by an external luer connector and allows repeated withdrawal of the liquid medicament from the vial without risk of contamination from atmospheric environment.

This embodiment of the present invention wherein the pair of spikes are centered ensures alignment with the external luer connector and prevents buckling of the spikes upon insertion into the a rubber stopper.

DETAILED DESCRIPTION OF THE INVENTION

Figure 1:
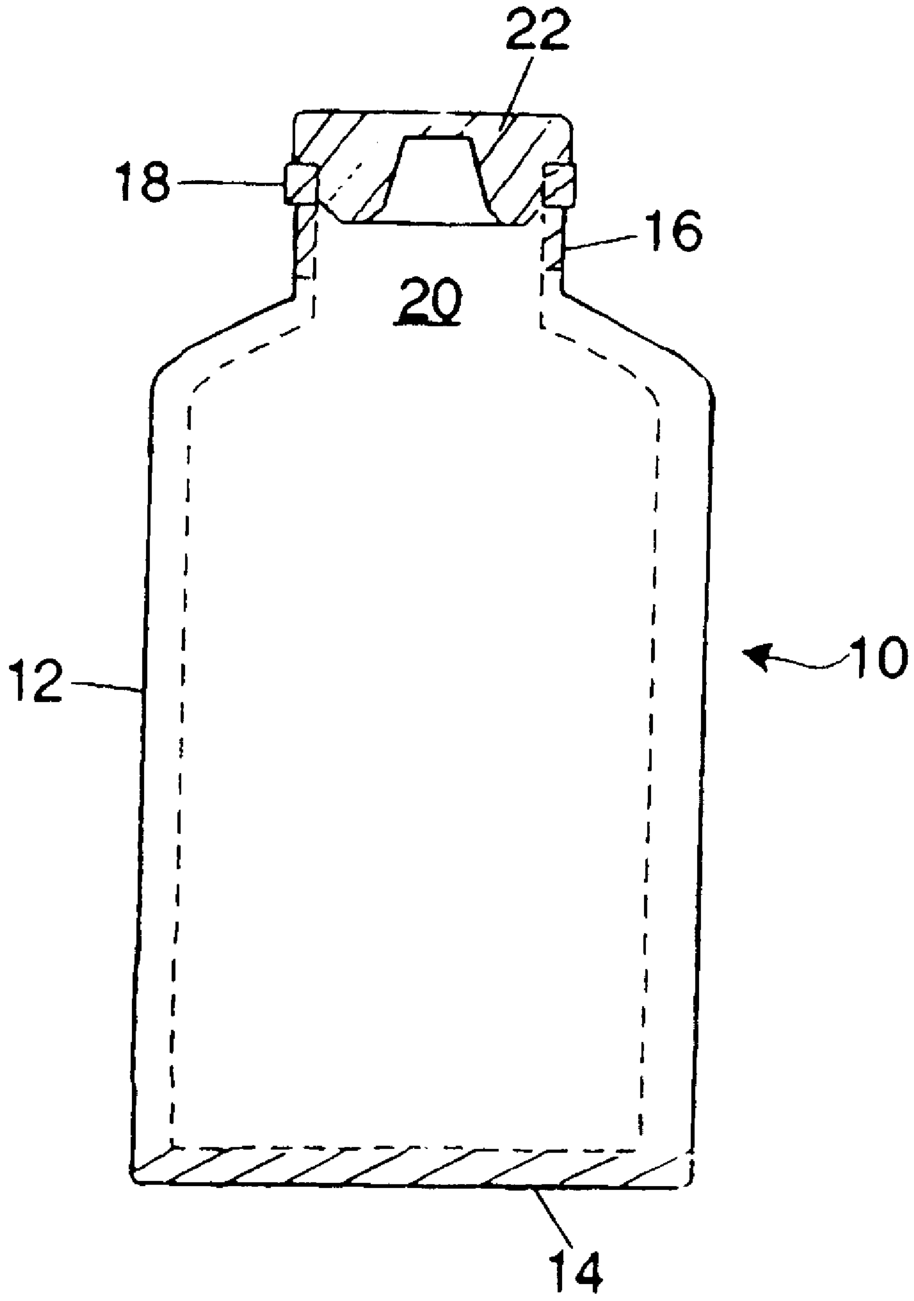
FIG. 1 is a cross-section of a typical vial used in conjunction with the vial access adapter of the present invention.

The vial access adapter of the present invention is used in conjunction with containers such as vials containing a fluid medicament therein, such as parenteral solutions and diagnostic media. Referring to the drawings, FIG. 1 shows the cross-section of vial 10 in an upright position having: a cylindrical side wall 12, a flat bottom portion 14 so that it may be placed in normal upright position on any flat surface, and a constricted neck portion 16 terminating in a rim 18. The neck portion and rim define an open area 20 closed by stopper 22 hermetically sealing the content of the vial. Typically, the stopper is held in the vial by a metal band (not shown).

Figure 2:
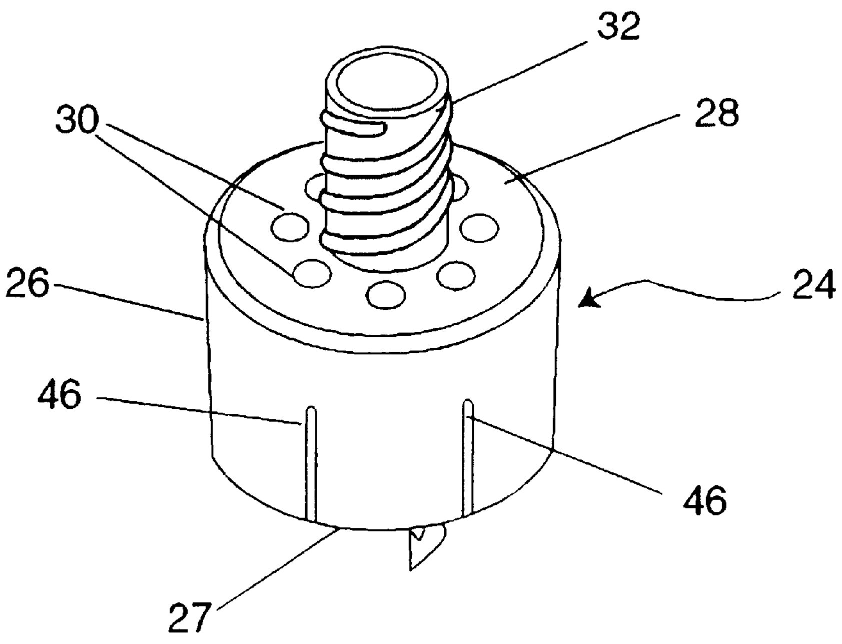
FIG. 2 is a perspective view of the first embodiment of the vial access adapter showing the cylindrical side wall, flat top portion with vent holes, and threaded luer connector means rising above the flat top portion.
Figure 3:
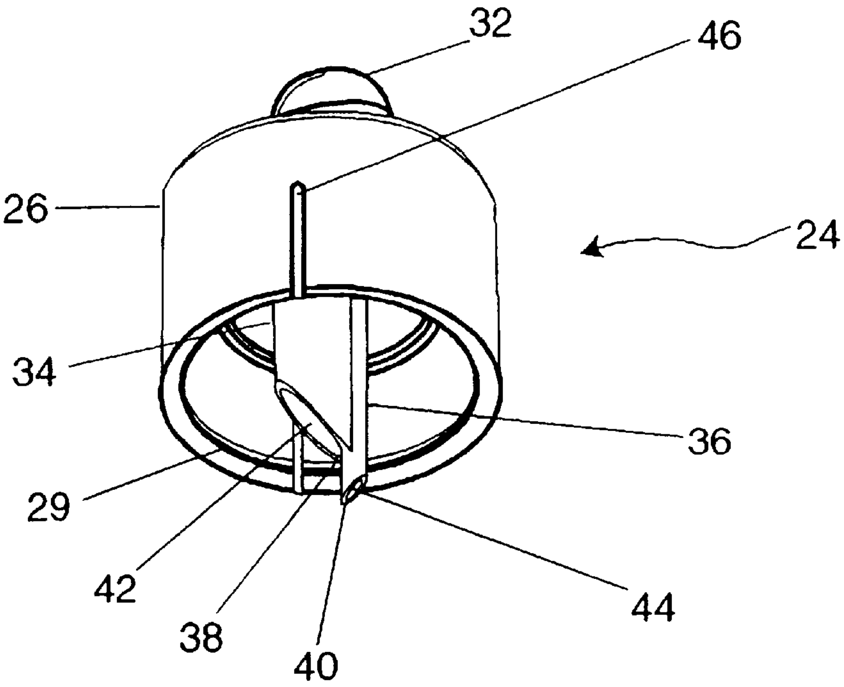
FIG. 3 is a another perspective view of the vial access adapter showing the cylindrical side wall, and the dual spike terminating in piercing sharp points.

The present invention comprises a first embodiment and a second embodiment. In reference to the first embodiment, the vial access adapter, generally designated by the numeral 24 and shown in perspective views in FIGS. 2 and 3, comprises: a cylindrical side wall 26 terminating in a rim 27; a flat, horizontal top wall 28 having vent holes 30 therein; threaded luer connector means 32 projecting vertically above the horizontal top wall 28; and a dual spike 34 and 36 terminating in sharp points 38 and 40 extending parallel to each other, and having flow passages therein 42 and 44, one being designed for passage of medicament, and the other being designed for passage of air. Cylindrical side wall 26 of the vial access adapter 24 is preferably provided with a plurality of slots 46 to facilitate the positioning of the vial access adapter onto vial 10 by a snap-on motion. In order to securely hold the vial access adapter on the vial, rim 27 of cylindrical sidewall 26 is provided with protuberance 29 projecting towards dual spike 34 and 36. Protuberance 29 engages the neck portion 16 just below rim portion 18 of vial 10.

Figure 4:
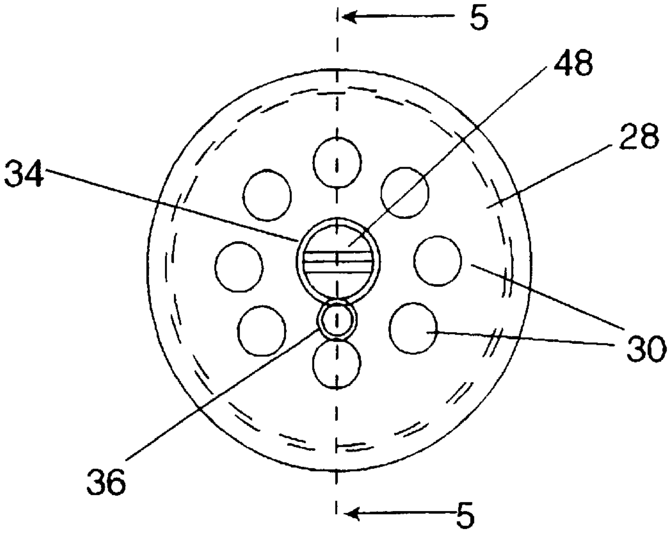
FIG. 4 is a top plan view of the vial access adapter.
Figure 5:
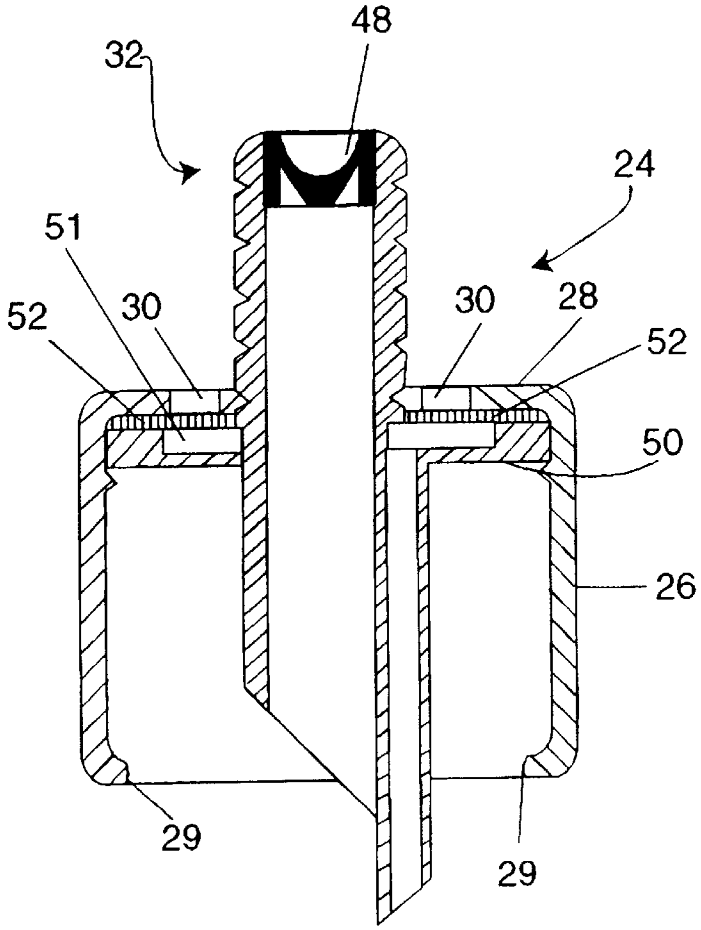
FIG. 5 is a cross-sectional view of the vial access adapter, having an M-shaped member therein, taken along the line 5—5 of FIG. 4.
Figure 5A:
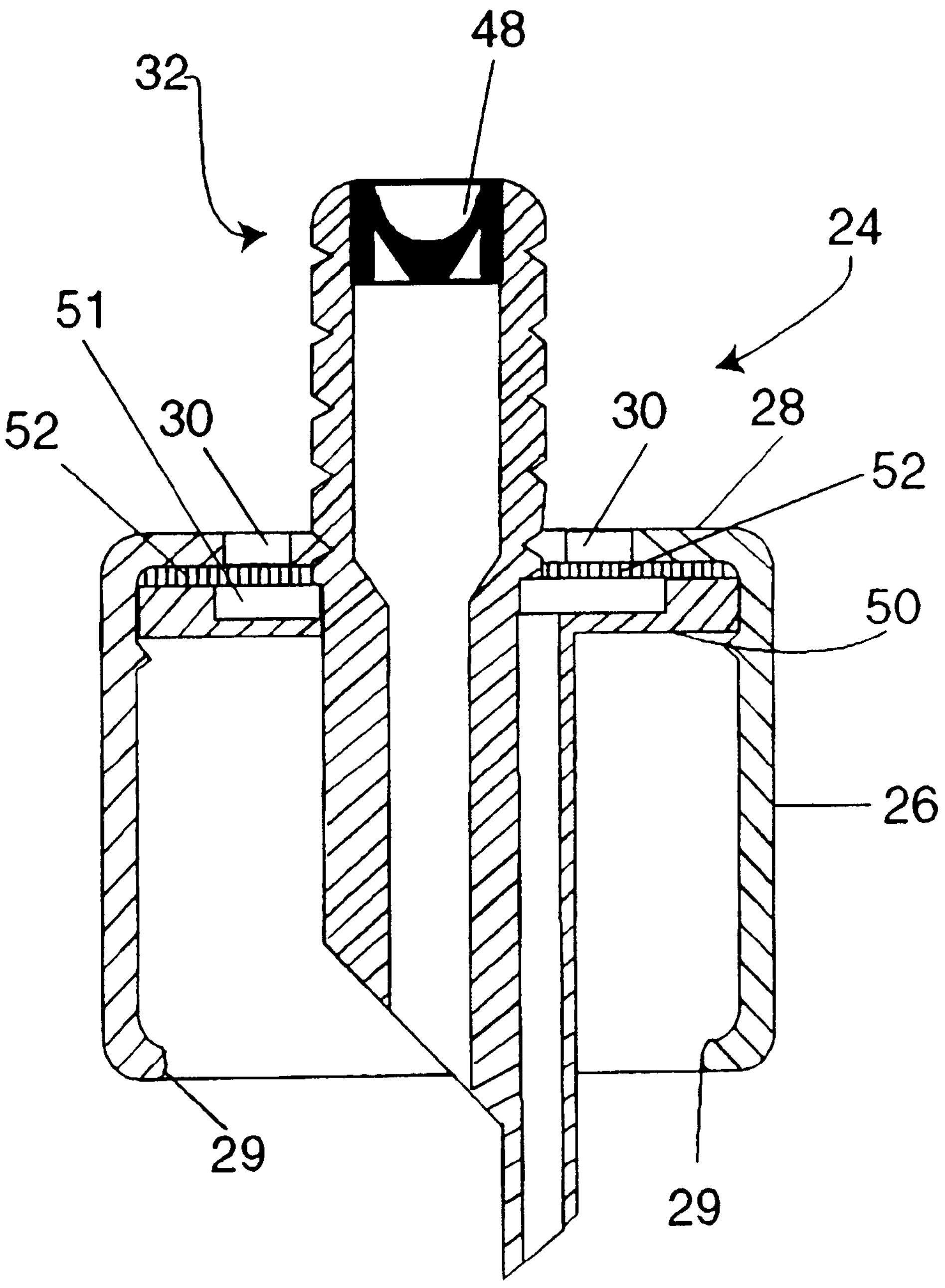
FIG. 5A is a cross-sectional view of the vial access adapter wherein the lower portion of the fluid flow channel had a reduced diameter.

Reference is now made to FIGS. 4 and 5. FIG. 4 shows a top plan view of the vial access adapter and FIG. 5 shows a cross-sectional view of the vial access adapter taken along the line 5—5 of FIG. 4.

In FIG. 4 there are shown: eight vent holes 30 in the flat, horizontal top wall 28, dual spike 34 and 36, and an elastomeric seal 48 positioned inside the threaded luer connector means.

As best seen in FIG. 5, the vial access adapter 24 further comprises an internal second wall 50 which is parallel to the flat, horizontal top wall 28 and is spaced therefrom. Flat, horizontal top wall 28, internal second wall 50, and cylindrical sidewall 26 enclose a chamber 51 therebetween designed to hold a filter 52. The filter is an anti-microbial filter known in the art, such as Whatman Grade HCO1, USP Class 6.

The anti-microbial filter is a circular mat of randomly oriented fibers bound together with a polymeric material, such as a polyester elastomers, ethylene methacrylate, ethylene vinyl acetate, ethylene vinyl alcohol, polyethylene and polypropylene treated with an anti-bacterial agent. The randomly oriented fibers may be made of nylon, cellulose, rayon and polyester.

One of the dual spikes 34 is adapted to carry liquid medicament from vial 10. This spike is integral with the threaded luer connector means 32 and passes through the flat, horizontal top wall 28, and internal second wall 50. When the vial access adapter is assembled with vial 10 and pierces stopper 22, sharp point 38 just clears the bottom surface of stopper 22 to reach the liquid medicament contained in the vial. In use, when the vial is turned upside-down and connected to the vial access adapter, this positioning of the sharp point 38 just below the bottom surface of the stopper allows for maximum amount of withdrawal of medicament from the vial.

The other of the dual spike 36 runs parallel to spike 34, however it only runs from below chamber 51 and is connected to internal second wall 50 and terminates in sharp point 40. It extends into the vial somewhat below sharp point 38 of first spike 34 so that atmospheric air can be introduced into the vial even when the content of the vial is at a minimum volume.

Figure 5B:
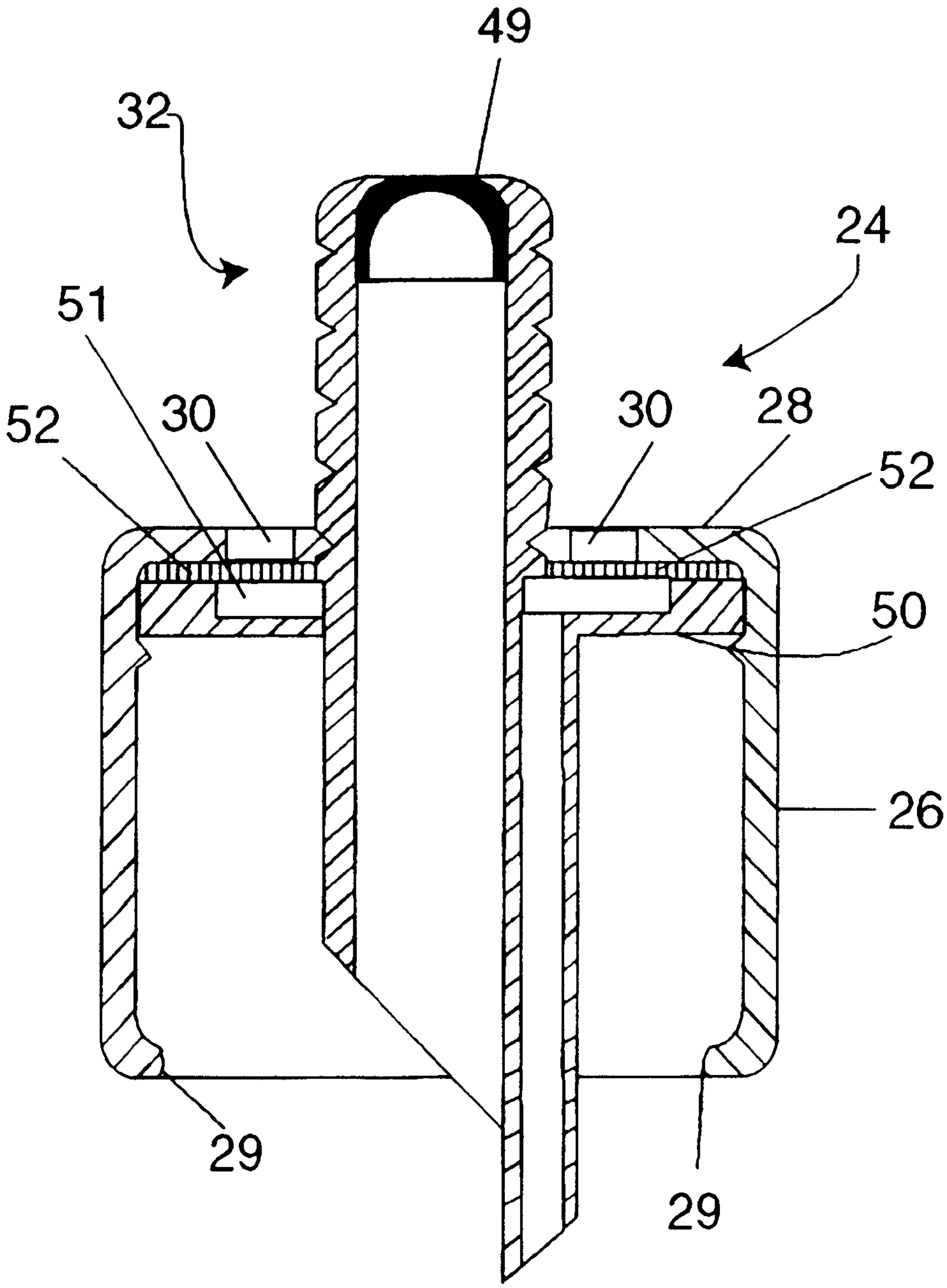
FIG. 5B is a cross-sectional view of the vial access adapter wherein the membrane is of an inverted U-shaped configuration.

The vial access adapter can be used without a seal within the threaded luer connector means 32. Preferably, however, a seal is used to prevent entry of atmospheric air when the vial access adapter is placed on the vial containing a medicament. The seal can be a horizontal, flat elastomeric membrane, or an inverted U-shaped membrane 49 as shown in FIG. 5B, which can be ruptured by a luer connector. Most preferably, the seal is an M-shaped elastomeric seal or membrane shown in FIGS. 5, 5A, 6, 7 and 8 which is capable of resealing itself after one or more puncture by a luer connector.

The M-shaped elastomeric seal or membrane 48 is of inert, gas-impermeable polymeric material capable of flexing under pressure. It preferably has a thickness of from about 0.001 mm to about 1.00 mm and a durometer of from about 25 to about 80 Shore A. It is capable of being ruptured by a twisting motion of a luer connector. The configuration of the elastomeric membrane is M-shaped having vertical leg portions and a top surface resembling a cup shape. Suitable elastomeric materials for constructing the diaphragm include:

- natural rubber;
- acrylate-butadiene rubber;
- cis-polybutadiene;
- chlorobutyl rubber;
- chlorinated polyethylene elastomers;
- polyalkylene oxide polymers;
- ethylene vinyl acetate;
- fluorosilicone rubbers;
- hexafluoropropylene-vinylidene fluoride-tetrafluoroethylene terpolymers such as sold under the tradenames of Fluorel and Viton;
- butyl rubbers;
- polyisobutene, such as sold under the tradename Vistanex;
- synthetic polyisoprene rubber;
- silicone rubbers;
- styrene-butadiene rubbers;
- tetrafluoroethylene propylene copolymers; and
- thermoplastic-copolyesters.

Figure 6:
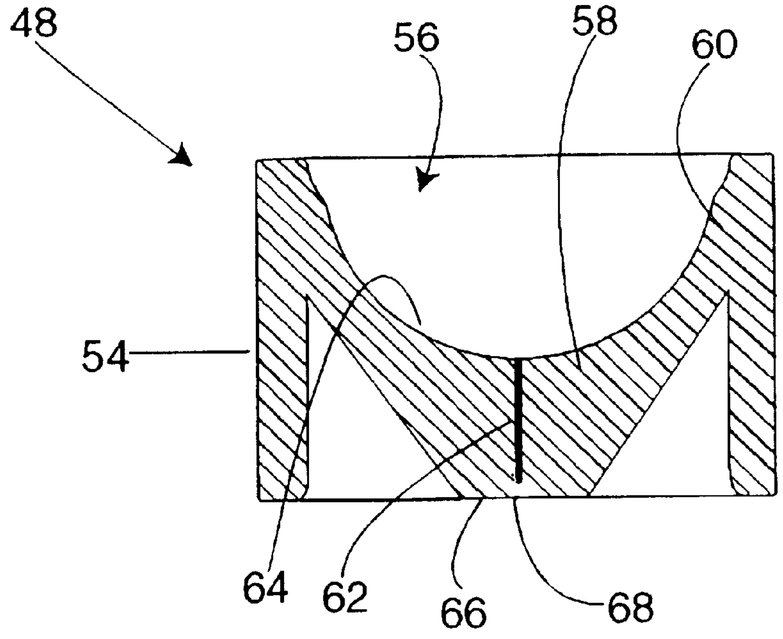
FIG. 6 shows an elastomeric seal in the form of the M-shaped membrane.
Figure 7:
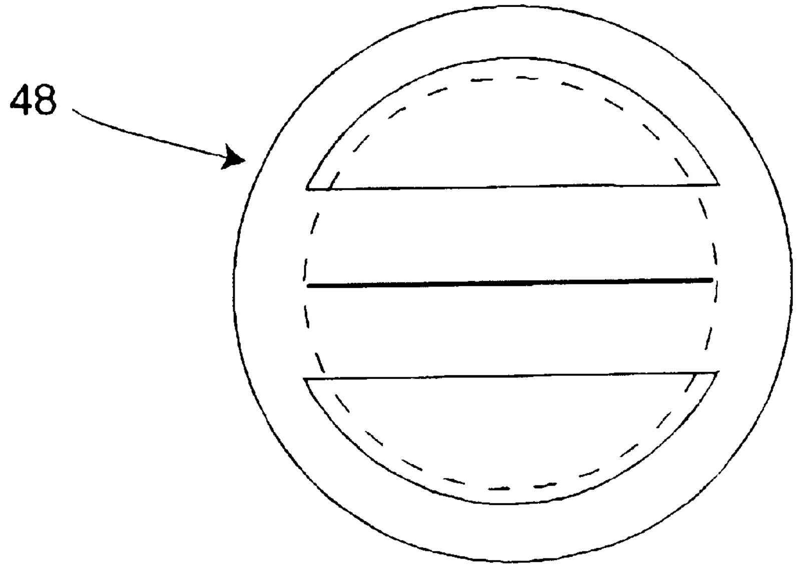
FIG. 7 is a top plan view of the M-shaped membrane shown in FIG. 6.

As best seen in FIGS. 6 and 7, the M-shaped membrane 48 comprises: leg portion 54, and cup-shaped portion 56. Cup-shaped portion comprises: horizontal bottom portion 58; and side portion 60. Leg portion 54 and side portion 60 typically have a thickness of from about 3 to 6 mm while bottom portion 58 typically has a thickness of from about 5 to 20 mm.

The horizontal bottom portion 58 is provided with a slit 62 which extends from the top surface 64 of the horizontal bottom portion toward the bottom surface 66. However, the slit does not penetrate the bottom surface. The unpenetrated membrane, denoted by the numeral 68, has a thickness of from about 0.001 mm to about 2.0 mm. The unpenetrated membrane maintains the content of the container in sealed condition. In use, when this membrane is ruptured by an external access means, such as a luer connector or spike, fluid communication is established between the content of the container and the external access means. Upon disengaging the external access means, the cup-shaped portion of the diaphragm reseals itself for the reason that the membrane is resilient and springs back to its original configuration. As a result, the container is resealed until the fluid withdrawal process is repeated.

The M-shaped membrane is bounded to the medicament-carrying spike 34 at its opening thereof by conventional means known in the art.

Figure 8:
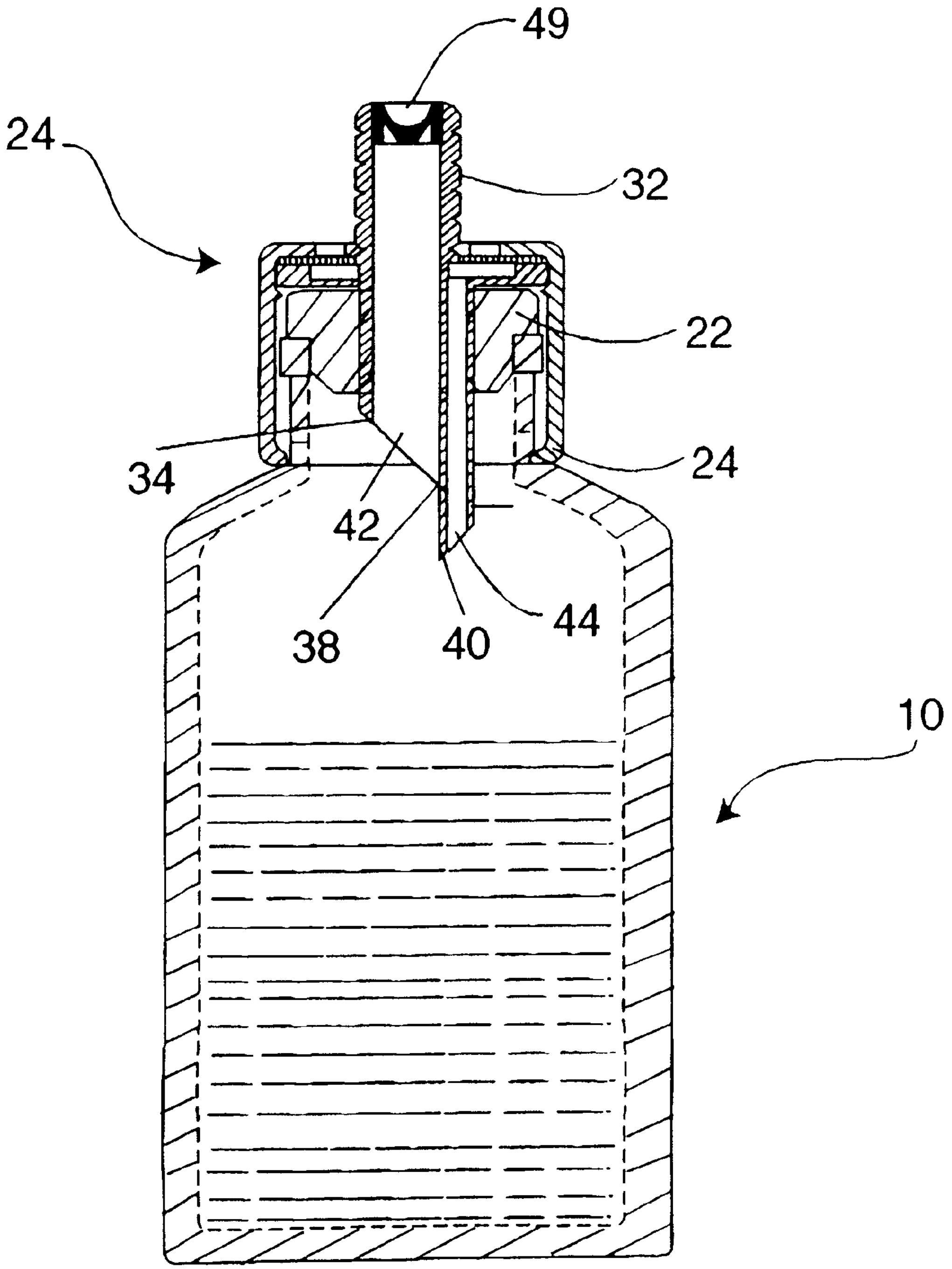
FIG. 8 shows the vial access adapter assembled with the vial.

FIG. 8 shows in cross-sectional view the vial access adapter 24 and the vial 10 assembly. Dual spikes 34 and 36 have been inserted into the vial through stopper 22. Liquid medicament passage 42 just clears the bottom portion of the stopper so that, when the assembly is turned upside-down, essentially all the liquid medicament may be withdrawn from the vial.

Spike 36 having air-flow passage 44 therein is longer than spike 34 having liquid medicament flow passage 42 therein in order to prevent air from circulating back into the liquid medicament flow passage during withdrawal of the liquid medicament from the vial.

Figure 9:
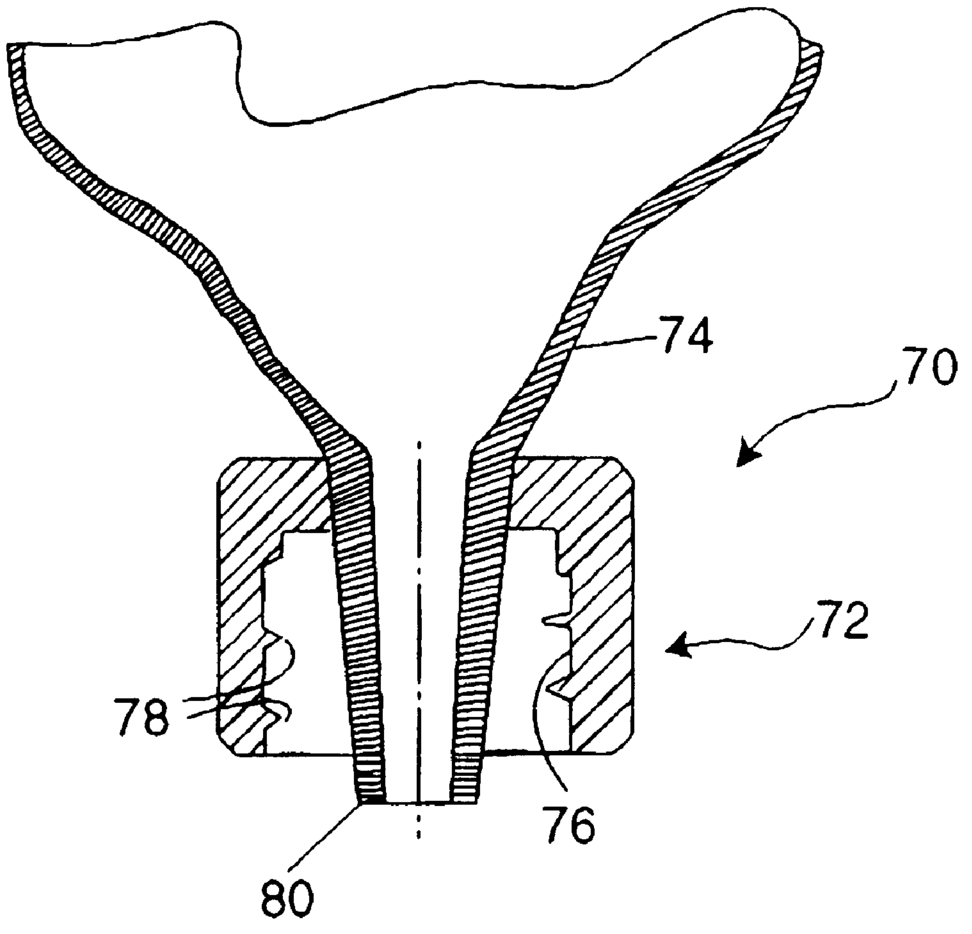
FIG. 9 illustrates a luer connector attachable to the vial access adapter.

FIG. 9 shows in cross-sectional view a typical luer connector 70 attachable to the vial access adapter of the present invention. The luer connector comprises a cylindrical cap 72 and a tubing conduit 74. Cylindrical cap 72 comprises inside wall 76 having threads 78 therein extending towards tubing conduit 74. Upon attachment, luer connector 70 will engage thread means 32 of vial access adapter 24. Tubing conduit 74 has a bottom portion 80 which extends beyond the cylindrical cap and is adapted to rupture the elastomeric membrane 48 or 49 of the vial access adapter 24.

Figure 10:
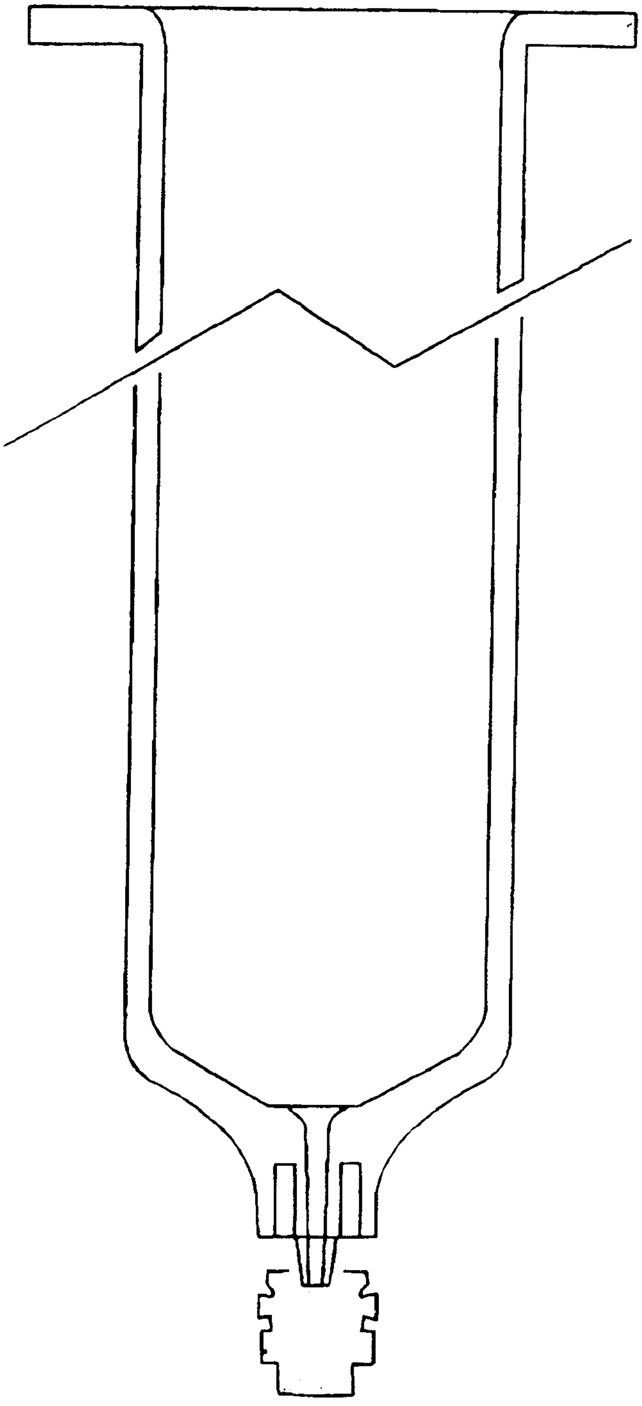
FIG. 10 illustrates, in a cross-sectional view, a portion of the threaded luer connector prior to penetration of a membrane by the luer connector of a syringe.

FIG. 10 shows in cross-sectional view a portion of the threaded luer connector means with the elastomeric membrane therein prior to penetration of the membrane by the luer connector of a syringe.

Figure 11:
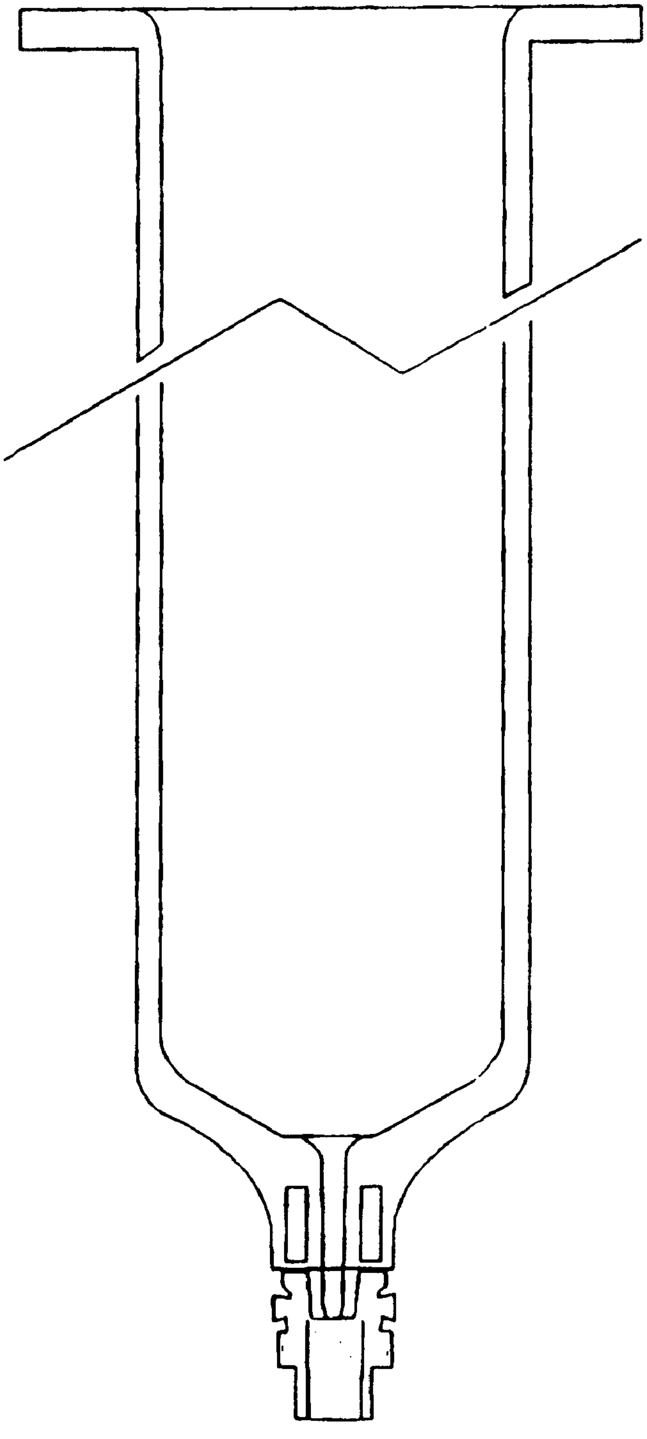
FIG. 11 illustrates, in a cross-sectional view, a portion of the threaded luer connector during penetration and breakthrough of the membrane by the luer connector of the syringe.

FIG. 11 shows in cross-sectional view a portion of the threaded luer connector means with the elastomeric membrane therein during penetration and break-through of the membrane by the luer connector of a syringe.

Figure 12:
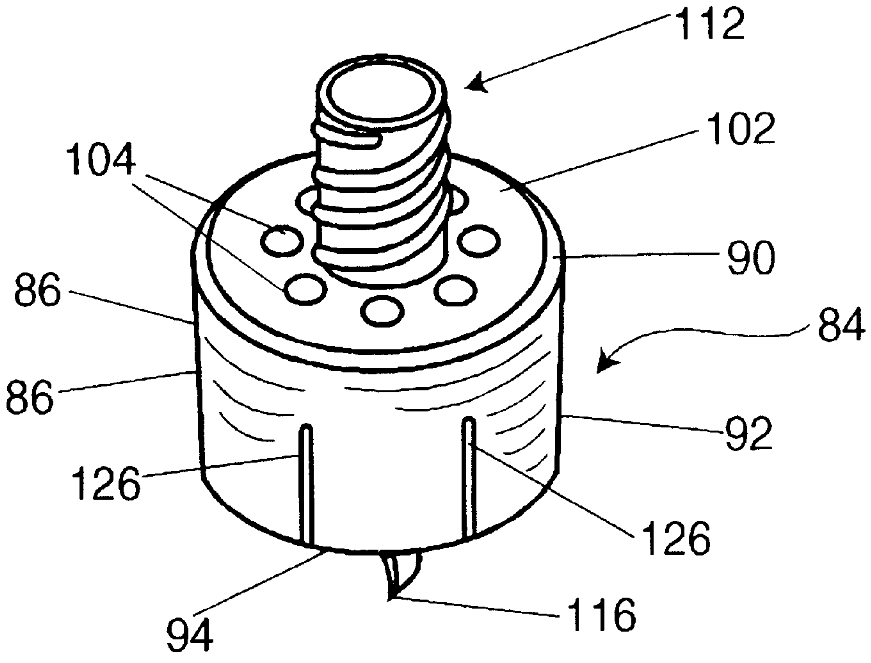
FIG. 12 is a perspective view of the second embodiment of the vial access adapter showing the cylindrical side wall, flat top portion with vent holes, and threaded luer connector means rising above the flat top portion.
Figure 13:
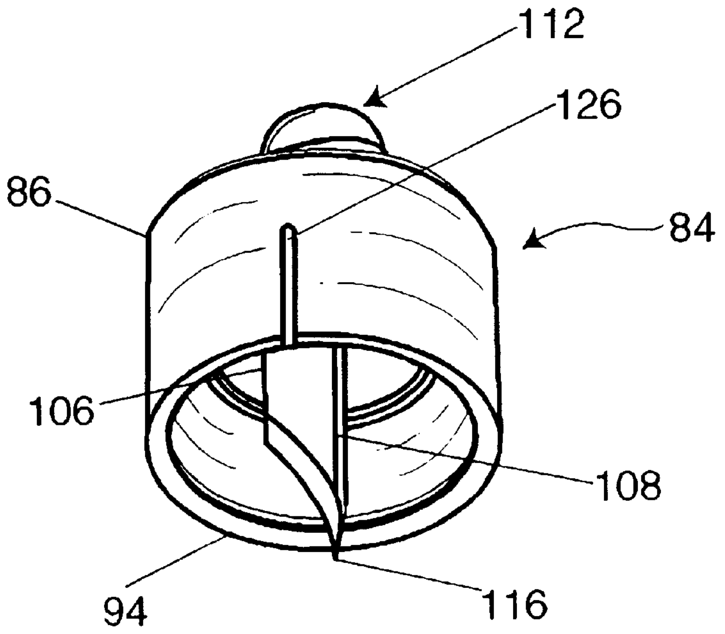
FIG. 13 is another perspective view of the second embodiment of the vial access adapter showing the cylindrical side wall, and the dual spike terminating in a piercing sharp point wherein the piercing sharp point is formed by the fluid and air tubes merging together and the fluid and air tubes together are positioned in the center of the vial access adapter.
Figure 14:
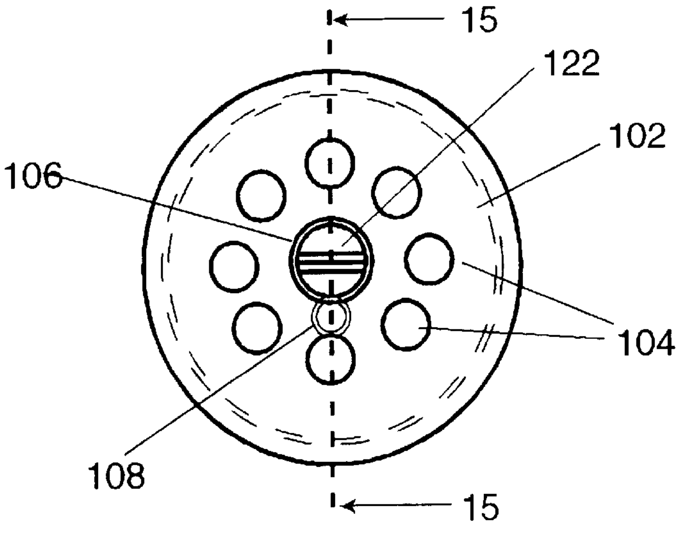
FIG. 14 is a top plan view of the vial access adapter.
Figure 15:
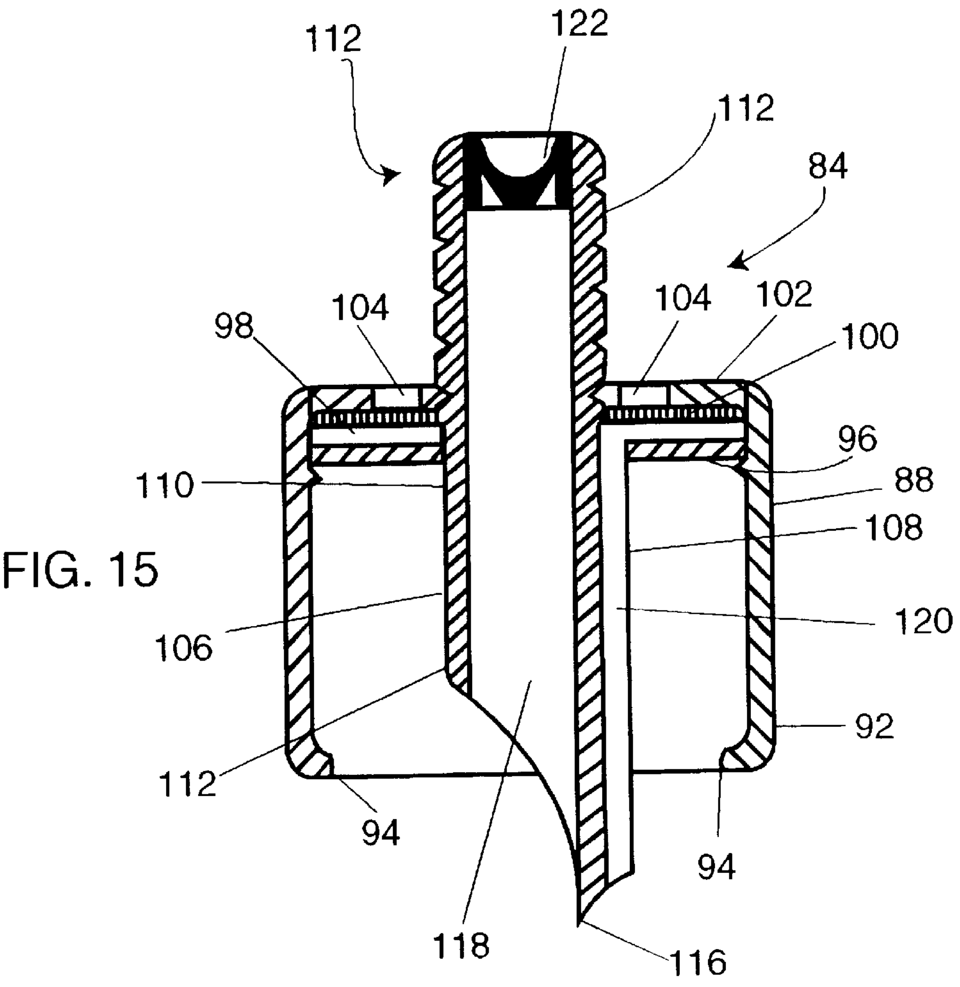
FIG. 15 is a cross-sectional view of the vial access adapter, having an M-shaped member therein, taken along the line 15—15 of FIG. 14.
Figure 15A:
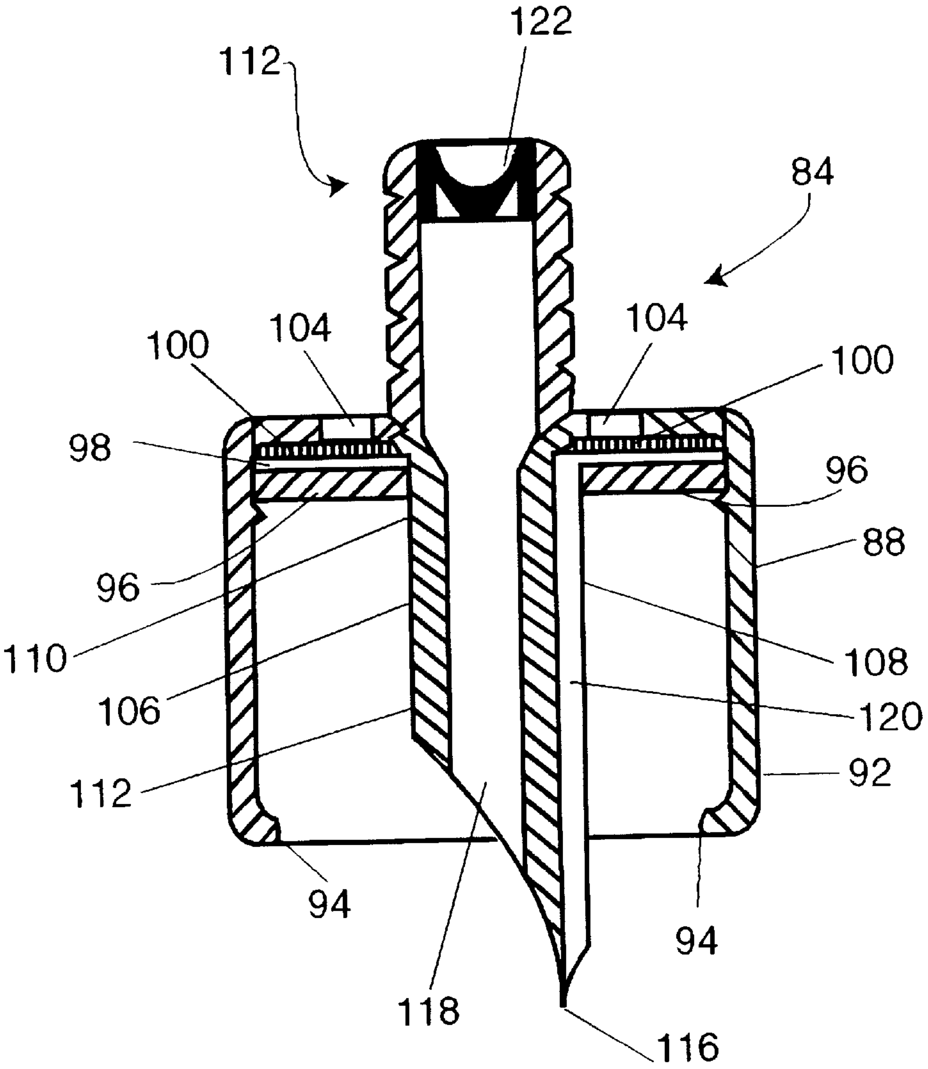
FIG. 15A is a cross-sectional view of the vial access adapter wherein the lower portion of the fluid flow channel has a reduced diameter.
Figure 15B:
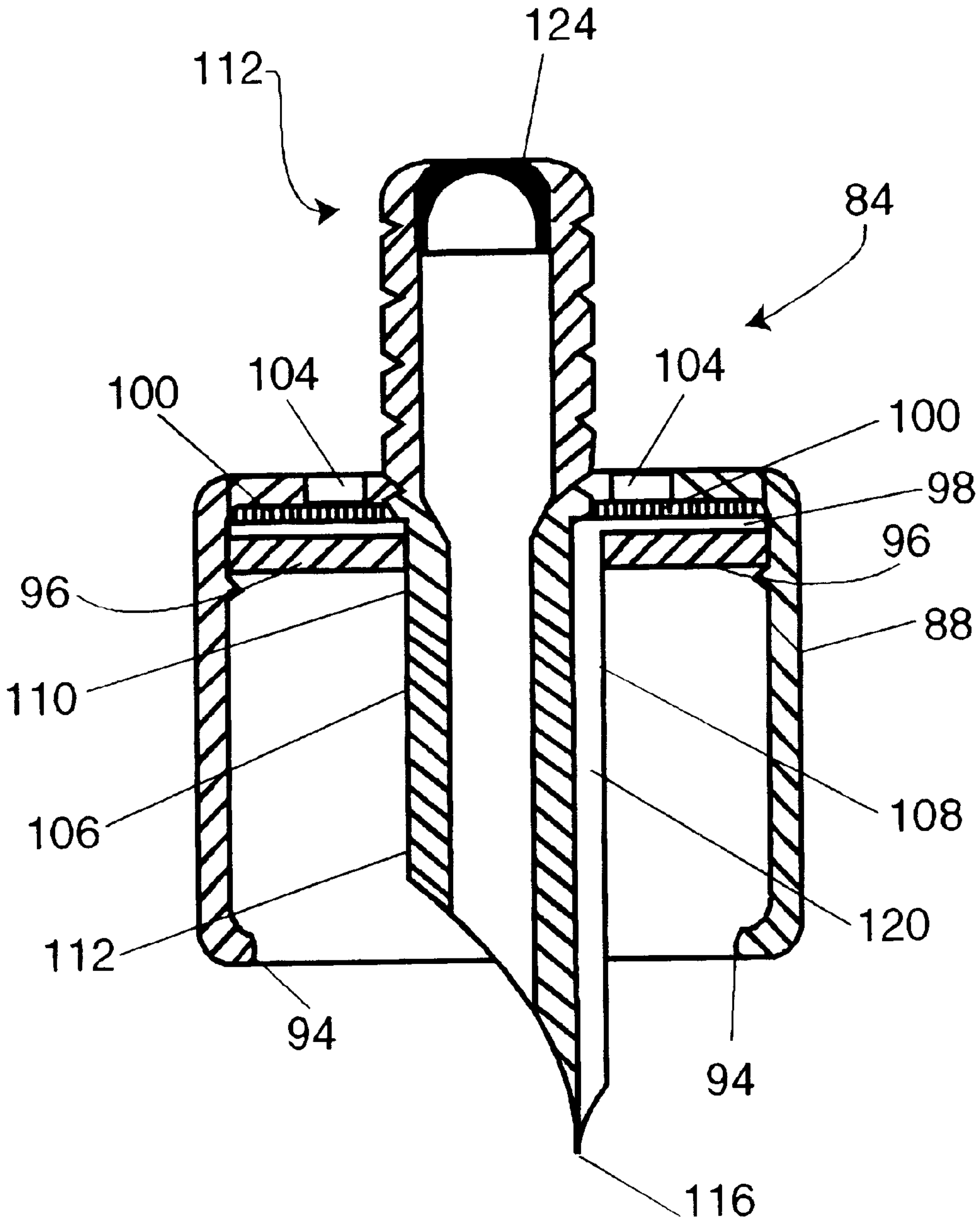
FIG. 15B is a cross-sectional view of the vial access adapter wherein the membrane is of an inverted and U-shaped configuration.

FIGS. 12, 13, 14, 15, 15A and 15B show the second embodiment of the present invention wherein: FIGS. 12 and 13 are perspective views of the vial access adapter; FIG. 14 is a top plan view thereof; FIG. 15 is a cross-sectional view of the vial access adapter taken along the line 15—15 of FIG. 14; FIG. 15A is a cross-sectional view of the vial access adapter wherein the lower portion of the fluid flow channel has a reduced diameter; and FIG. 15B is a cross-sectional view of the vial access adapter wherein the membrane is of an inverted U-shaped configuration.

In this embodiment the vial access adapter body generally designated by the numeral 84 comprises:

- a cylindrical side wall 86 having a top portion 88 terminating in a top rim 90, and a skirt portion 92 extending downward from top rim 90 and terminating in a bottom rim 94;
- a horizontal, circular wall 96 enclosing the top portion 88 of the cylindrical side wall 86 located slightly below top rim 90 and forming a disc-shaped chamber 98 with top rim 90;
- a disc-shaped anti-bacterial filter 100 positioned in disc-shaped chamber 98;
- a removable retaining disc 102 for retaining the anti-bacterial filter 100, positioned on the top of the anti-bacterial filter, covering the disc-shaped chamber and is horizontally aligned with top rim 90;
- a plurality of vent holes 104 in the removable retaining disc 102 to allow entry of atmospheric air into the disc-shaped anti-bacterial filter 100;

- a pair of spikes 106 and 108 integral with each other, centrally located in the vial access adapter body: the first spike 106 of the pair having a top portion 110 extends above the horizontal, circular wall 96 terminating in an externally threaded luer connector 112, and the bottom portion 114 extending downward terminating slightly below bottom rim 94 of skirt portion 92; and a second spike 108 of the pair extends from the horizontal, circular wall 96 downward toward the bottom rim 94 of the skirt portion 92 and terminates slightly below the bottom rim 94, wherein the pair of spikes 106 and 108 terminate in a sharp point 116;
- a fluid flow channel 118 in first spike 106 of the pair designed to carry a liquid medicament from a vial to which the vial access adapter is attached;
- an air flow channel 120 in the second spike 108 of the pair designed for allowing atmospheric air flow through the disc-shaped chamber 98 and anti-bacterial filter 100 into the vial during withdrawal of the liquid medicament from the vial; and
- an elastomeric membrane 122 or 124 within the luer connector 112 of the first spike 106 of the pair for sealing the fluid flow channel.

A plurality of slits 126 is provided in the bottom portion of the skirt to facilitate the positioning of the vial access adapter onto the vial.

This second embodiment of the present invention provides certain desirable features over the first embodiment. The fluid flow spike and the air flow spike are integral with each other and are stronger than would be if separated thereby preventing buckling of the spikes upon insertion into a stopper. The dual, integral spikes are centered with respect to the luer port to ensure proper mounting on the vial. The manufacturing of the vial access adapter is more economical since the two parts, the retaining disc and the body of the vial access adapter, are manufactured separately without the presence of the anti-bacterial filter. Installation of the anti-bacterial filter is made easy by placing the anti-bacterial filter into the disc-shaped chamber and then installing the removable retaining disc thereon by a snapping motion.

In use, the vial access adapter of both embodiments is engaged with a vial containing a liquid medicament therein by a snap-on motion. The dual spike penetrates the stopper establishing fluid communication between the vial and the vial access adapter. Next, an external connector or the luer connector of a syringe is engaged with the vial access adapter by a twisting motion, threading the luer connector into the luer connector means of the vial access adapter. Upon sufficient twisting the elastomeric membrane is ruptured and fluid communication is achieved between the luer connector and the vial access adapter. These steps of engagement are accomplished while the vial containing the liquid medicament is positioned on a flat surface in a rightside-up position. Upon completing these steps, the vial is turned upside-down and the liquid medicament is transferred from the vial into the external luer connector having tubing conduit therein from which the medicament is administered to a patient. When a syringe, having a plunger therein equipped with a luer connector is used, withdrawal of the liquid medicament is accomplished by moving the plunger towards its open end and thereby drawing the liquid medicament into the syringe barrel. The desired amount of liquid medicament withdrawn can be seen in the syringe. Upon disconnecting the external luer connector from the vial access adapter, the M-shaped elastomeric membrane reseals itself thereby keeping the liquid medicament in the vial in aseptic condition. The self-sealing membrane allows repeated access to the liquid medicament contained in the vial.

The vial access adapter body is made of rigid or semi-rigid polymeric materials and can be used on bottles and vials made of glass or rigid or semi-rigid polymeric materials. The liquid medicament contained in the bottles and vials can be a therapeutic, a diagnostic, or a nutritional preparation.

LIST OF REFERENCE NUMBERS USED

| | |
|---|---|
| Vial | 10 |
| Cylindrical side wall of vial | 12 |
| Flat bottom portion of vial | 14 |
| Neck portion of vial | 16 |
| Rim portion of top of vial | 18 |
| Open area of top portion of vial | 20 |
| Stopper | 22 |
| Vial access adapter | 24 |
| Cylindrical side wall of vial access adapter | 26 |
| Rim of cylindrical side wall | 27 |
| Flat horizontal top wall of vial access adapter | 28 |
| Protuberance on rim portion | 29 |
| Vent holes in top wall of vial access adapter | 30 |
| Threaded luer connector means | 32 |
| Dual spikes | 34 and 36 |
| Sharp points in dual spikes | 38 and 40 |
| Flow passages in dual spikes | 42 and 44 |
| Slots in cylindrical side wall | 46 |
| Elastomeric seal/membrane, M-shaped diaphragm | 48 |
| U-shaped diaphragm | 49 |
| Internal second wall | 50 |
| Chamber | 51 |
| Filter | 52 |
| Leg portion of M-shaped membrane | 54 |
| Cup-shaped portion of M-shaped membrane | 56 |
| Horizontal bottom portion of cup-shaped portion | 58 |
| Side portion of cup-shaped portion | 60 |
| Slit in bottom portion | 62 |
| Top surface of cup-shaped portion | 64 |
| Bottom surface of cup-shaped portion | 66 |
| Unpenetrated portion of membrane | 68 |
| Luer connector (external) | 70 |
| Cylindrical cap of luer connector | 72 |
| Tubing conduit of luer connector | 74 |
| Inside wall of cylindrical cap | 76 |
| Threads on inside wall of cylindrical cap | 78 |
| Bottom end portion of tubing conduit | 80 |
| Vial access adapter, generally designated | 84 |
| Cylindrical side wall of the vial access adapter | 86 |
| Top portion of cylindrical side wall | 88 |
| Top rim of cylindrical side wall | 90 |
| Skirt portion of cylindrical side wall | 92 |
| Bottom rim of skirt portion | 94 |
| Horizontal circular wall | 96 |
| Disc-shaped chamber | 98 |
| Disc-shaped anti-bacterial filter | 100 |
| Removable retaining disc | 102 |
| Plurality of vent holes in removable retaining disc | 104 |
| Pair of spikes: first spike and second spike | 106 & 108 |
| Top portion of first spike | 110 |
| Externally threaded luer connector, generally designated | 112 |
| Bottom portion of first spike 106 | 114 |
| Sharp point formed by the first and second spike | 116 |
| Fluid flow channel in first spike 106 | 118 |
| Air flow channel in second spike 108 | 120 |
| Elastomeric membrane | 122 & 124 |
| Plurality of slits in skirt portion | 126 |

Various modifications of the present invention disclosed will become apparent to those skilled in the art. This invention is intended to include such modifications to be limited only by the scope of the claims.

What is claimed is:

1. A vial access adapter for withdrawal of a fluid contained in a vial, said vial access adapter having a vial access adapter body comprising:

a vertical cylindrical side wall having a top portion terminating in a top rim, and a skirt portion extending downward from the top rim and terminating in a bottom rim;

a horizontal, circular wall enclosing the top portion of the vertical cylindrical side wall being located slightly below said top rim forming a disc-shaped chamber with said top rim;

a disc-shaped anti-bacterial filter positioned in said disc-shaped chamber;

a removable retaining disc having a plurality of vent holes therein positioned over said anti-bacterial filter and being pressed into said disc-shaped chamber;

a first spike and a second spike integral with each other centrally located in the vial access adapter body wherein: said first spike having a top portion extends above said horizontal, circular wall and is integral therewith and extends above said removable retaining disc terminating in an externally threaded luer connector, and a bottom portion extending downward terminating slightly below said bottom rim of the cylindrical side wall; said second spike extends downward from said horizontal, circular wall toward said bottom rim of the cylindrical side wall terminating slightly below said bottom rim of the cylindrical side wall, wherein said first spike and said second spike together terminate in one sharp point adapted to pierce an elastomeric stopper;

a fluid flow channel in said first spike adapted to carry a liquid medicament from a vial;

an air flow channel in said second spike adapted to carry atmospheric air from said disc-shaped chamber through said disc-shaped anti-bacterial filter into a vial; and an elastomeric membrane within said luer connector in said first spike for sealing said fluid flow channel.

2. The vial access adapter of claim 1 wherein said elastomeric membrane is of inverted U-shaped configuration.

3. The vial access adapter of claim 1 wherein said elastomeric membrane is of M-shaped configuration capable of flexing under pressure and re-sealing itself after being pierced by an external access means.

4. The vial access adapter of claim 1 wherein said elastomeric membrane has a thickness of from about 5 mm to about 20 mm, and a durometer of from about 25 to about 80 Shore A.

5. The vial access adapter of claim 1 wherein said elastomeric membrane is of an elastomeric material selected from the group consisting of natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene;

tetrafluoroethylene terpolymers;

butyl rubbers;

polyisobutene;

synthetic polyisoprene rubber;

silicone rubbers;

styrene-butadiene rubbers;

tetrafluoroethylene propylene copolymers; and thermoplastic-copolyesters.

6. The vial access adapter of claim 1 wherein said M-shaped elastomeric membrane comprises a leg portion and a cup-shaped portion.

7. The vial access adapter of claim 6 wherein said cup-shaped portion comprises a horizontal bottom portion having a top surface and a bottom surface and a slit therein extending from the top surface thereof towards the bottom surface thereof without penetrating said bottom surface.

8. The vial access adapter of claim 1 wherein said unpenetrated portion has a thickness of from about 0.001 to about 2.0 mm.

9. A vial access adapter-vial assembly comprising:

a) a vial having a medical fluid therein; and b) a vial access adapter body, wherein said vial comprises a fluid port closed by an elastomeric stopper hermetically sealing the medical fluid contained therein, said elastomeric stopper having a top surface and a bottom surface;

said vial access adapter body comprising:

a vertical cylindrical side wall having a top portion terminating in a top rim, and a skirt portion extending downward from the top rim and terminating in a bottom rim;

a horizontal, circular wall enclosing the top portion of the vertical cylindrical side wall being located slightly below said top rim forming a disc-shaped chamber with said top rim;

a disc-shaped anti-bacterial filter positioned in said disc-shaped chamber;

a removable retaining disc having a plurality of vent holes therein positioned over said anti-bacterial filter and being pressed into said disc-shaped chamber;

a first spike and a second spike integral with each other centrally located in the vial access adapter body wherein: said first spike having a top portion extends above said horizontal, circular wall and is integral therewith and extends above said removable retaining disc terminating in an externally threaded luer connector, and a bottom portion extending downward terminating slightly below said bottom rim of the cylindrical side wall; said second spike extends downward from said horizontal, circular wall toward said bottom rim of the cylindrical side wall terminating slightly below said bottom rim of the cylindrical side wall, wherein said first spike and said second spike together terminate in one sharp point adapted to pierce an elastomeric stopper;

a fluid flow channel in said first spike adapted to carry a liquid medicament from said vial;

an air flow channel in said second spike adapted to carry atmospheric air from said disc-shaped chamber through said disc-shaped anti-bacterial filter into said vial; and an elastomeric membrane within said luer connector in said first spike for sealing said fluid flow channel; wherein said one sharp point of said first spike and said second spike is pierced through said elastomeric stopper to establish fluid communication with said medical fluid contained in said vial and air flow communication from said disc-shaped chamber into said vial.

10. The vial access adapter-vial assembly of claim 9 wherein said elastomeric membrane is of inverted U-shaped configuration.

11. The vial access adapter-vial assembly of claim 9 wherein said one sharp point of said first spike and said second spike piercing said elastomeric stopper is essentially at the bottom surface of said elastomeric stopper.

12. The vial access adapter-vial assembly of claim 9 wherein said anti-bacterial filter is a circular mat of randomly oriented fibers bound together with a polymeric material selected from the group consisting of polyester elastomers, ethylene methacrylate, ethylene vinyl acetate, ethylene vinyl alcohol, polyethylene and polypropylene treated with an anti-bacterial agent.

13. The vial access adapter-vial assembly of claim 10 wherein said randomly oriented fibers are selected from the group consisting of nylon, cellulose rayon and polyester.

14. The vial access adapter-vial assembly of claim 9 wherein said elastomeric membrane is of M-shaped configuration capable of flexing under pressure and re-sealing itself after being pierced by an external access means.

15. The vial access adapter-vial assembly of claim 9 wherein said elastomeric membrane has a thickness of from about 5 mm to about 20 mm, and a durometer of from about 25 to about 80 Shore A.

16. The vial access adapter-vial assembly of claim 9 wherein said elastomeric membrane is of an elastomeric material selected from the group consisting of natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene;

tetrafluoroethylene terpolymers;

butyl rubbers;

polyisobutene;

synthetic polyisoprene rubber;

silicone rubbers;

styrene-butadiene rubbers;

tetrafluoroethylene propylene copolymers; and thermoplastic-copolyesters.

17. The vial access adapter-vial assembly of claim 14 wherein said M-shaped elastomeric membrane comprises a leg portion and a cup-shaped portion.

18. The vial access adapter-vial assembly of claim 17 wherein said cup-shaped portion comprises a horizontal bottom portion having a top surface and a bottom surface and a slit therein extending from the top surface thereof towards the bottom surface thereof without penetrating said bottom surface.

19. The vial access adapter-vial assembly of claim 18 wherein said unpenetrated portion has a thickness of from about 0.001 to about 2.0 mm.

20. The vial access adapter-vial assembly of claim 9 wherein said vial is of glass or polymeric material.

21. The vial access adapter-vial assembly of claim 9 wherein said medical fluid is selected from the group consisting of a therapeutic, diagnostic and nutritional preparation.

* * * * *

UNITED STATES PATENT AND TRADEMARK OFFICE

CERTIFICATE OF CORRECTION

PATENT NO. : 6,503,240 B1

DATED : February 20, 2004
INVENTOR(S) : Niedospial, Jr. et al.

It is certified that error appears in the above-identified patent and that said Letters Patent is hereby corrected as shown below:

Title page,
Item [73], Assignees name "Brocco Diagnostics, Inc., Princeton NJ (US)" should read -- Bracco Diagnostics, Inc., Princeton NJ (US) --

Signed and Sealed this

Thirteenth Day of April, 2004

JON W. DUDAS
*Acting Director of the United States Patent and Trademark Office*